United States Patent
Kerob et al.

(10) Patent No.: US 10,328,094 B2
(45) Date of Patent: Jun. 25, 2019

(54) COMPOUND FROM THE AVERMECTIN FAMILY FOR TREATING AND/OR PREVENTING FOLLICULITIS

(71) Applicant: GALDERMA SA, Cham (CH)

(72) Inventors: Delphine Kerob, La Defense (FR); Peter Arne Gerber, Dusseldorf (DE)

(73) Assignee: GALDERMA SA, Cham (CH)

( * ) Notice: Subject to any disclaimer, the term of this patent is extended or adjusted under 35 U.S.C. 154(b) by 0 days.

(21) Appl. No.: 15/550,643

(22) PCT Filed: Feb. 11, 2016

(86) PCT No.: PCT/EP2016/052885
§ 371 (c)(1),
(2) Date: Aug. 11, 2017

(87) PCT Pub. No.: WO2016/128499
PCT Pub. Date: Aug. 18, 2016

(65) Prior Publication Data
US 2018/0028547 A1  Feb. 1, 2018

(30) Foreign Application Priority Data
Feb. 12, 2015 (FR) .................... 15 51162

(51) Int. Cl.
*A61K 31/7048* (2006.01)
*A61K 9/00* (2006.01)
*A61K 31/517* (2006.01)
*A61K 39/00* (2006.01)
*A61K 45/06* (2006.01)
*A61K 31/4184* (2006.01)
*A61K 31/4523* (2006.01)
*A61K 31/519* (2006.01)

(52) U.S. Cl.
CPC ........ *A61K 31/7048* (2013.01); *A61K 9/0014* (2013.01); *A61K 31/4184* (2013.01); *A61K 31/4523* (2013.01); *A61K 31/517* (2013.01); *A61K 31/519* (2013.01); *A61K 39/00* (2013.01); *A61K 45/06* (2013.01)

(58) Field of Classification Search
CPC .......................... A61K 9/0014; A61K 31/7048
See application file for complete search history.

(56) References Cited

U.S. PATENT DOCUMENTS 5,952,372 A    9/1999  McDaniel
2015/0011489 A1  1/2015  Jacovella

OTHER PUBLICATIONS

Tsimboukis, S. et al "Erlotinib-induced skin rash in patients . . . " Clin. Lung Cancer, vol. 10, No. 1, pp. 106-111. (Year: 2009).*
Gerber, P. et al "Rosacea: the cytokine and chemokine network" J. Invest. Dermatol. Symp. Proc., vol. 15, pp. 40-47. (Year: 2011).*
Balagula, Y. et al "Dermatologic side effects associated with the MEK 1/2 inhibitor . . . " Invest. New Drugs, vol. 29, pp. 1114-1121. (Year: 2011).*
Zuniga, R. et al "Skin conditions: emerging drug-resistant . . . " FP Essent., vol. 407, pp. 17-23 (abstract only). (Year: 2013).*
Zuniga, R. et al "Skin conditions: emergent drug-resistant skin infections . . . " FP Essentials, vol. 407, pp. 17-23. (Year: 2013).*
International Search Report and English translation dated Apr. 21, 2016 corresponding to International Patent Application No. PCT/EP2016/052885, 8 pages.
Damian, D., et al., "Demodex Infestation in a child with leukaemia: treatment with ivermectin and permethrin," International Journal of Dermatology, Sep. 2003, vol. 42, No. 9, pp. 724-726.
Cotliar, J., et al., "Demodex Folliculitis Mimicking Acute Graft-vs-Host Disease," JAMA Dermatology, Dec. 2013, vol. 149, No. 12, pp. 1407-1409.
Stein Gold, L., et al., "Efficacy and Safety of Ivermectin 1% Cream in Treatment of Papulopustular Rosacea: Results of Two Randomized, Double-Blind, Vehicle-Controlled Pivotal Studies," Journal of Drugs in Dermatology, Mar. 2014, vol. 13, No. 3, pp. 316-323.
Bragg, J., et al., "Papulopustular drug eruption due to an epidermal growth factor receptor inhibitors, erlotinib and cetuximab," escholarship.org, Dermatology Online Journal, 2007, vol. 13, No. 1, XP-002751894, 1 page.
Gerber, P.A., et al., "Density of Demodex folliculorum in Patient s Receiving Epidermal Growth Factor Receptor Inhibitors," Dermatology, Jan. 2011, vol. 222, No. 2, pp. 144-147.
Patrizi, A., et al., "Rosaceiform eruption induced by erlotinib," Dermatologic Therapy, Oct. 2008, vol. 21 Suppl 2, pp. S43-S45.
Segaert, S., et al., "Skin toxicities of targeted therapies," European Journal of Cancer, Sep. 2009, vol. 45, pp. 295-297.
Laing, M.E., et al., "Eosinophilic pustular folliculitis induced by chemotherapy," J Am Acad Dermatol, Apr. 2006, vol. 54, No. 4, pp. 729-730.

\* cited by examiner

*Primary Examiner* — Leigh C Maier
(74) *Attorney, Agent, or Firm* — Sunit Talapatra; Foley & Lardner LLP (57) ABSTRACT

A compound from the avermectin family is described for use in treating and/or preventing folliculitis caused by anti-cancer agents and more particularly by agents for targeted therapy.

15 Claims, 5 Drawing Sheets

COMPOUND FROM THE AVERMECTIN FAMILY FOR TREATING AND/OR PREVENTING FOLLICULITIS

CROSS-REFERENCE TO PRIOR APPLICATIONS

This application is a National Stage of PCT/EP2016/052885, filed Feb. 11, 2016, and designating the United States (published on Aug. 18, 2016, as WO 2016/128449 A1), which claims priority under 35 U.S.C. § 119 to French Application No. 1551162, filed Feb. 12, 2015, each hereby expressly incorporated by reference in its entirety and each assigned to the assignee hereof.

The present invention relates to a compound of the avermectin family for use in the treatment and/or prevention of folliculitis caused by anti-cancer therapeutic agents and more particularly targeted-therapy agents.

TECHNICAL BACKGROUND

A very large number of toxic effects are associated with the use of anti-cancer therapeutic agents and in particular targeted-therapy agents. The toxic effects associated with these types of treatments are usually observed at the cutaneous level; they are in particular acneiform eruptions, xerosis, paronchia, alopecia or else inflammations of the mucous membranes. Acneiform eruptions, which include papulopustular eruptions or else folliculitis, are the toxic cutaneous effects most commonly observed in patients undergoing chemotherapy treatment and in particular targeted therapy, with an occurrence of approximately 80%. Folliculitis corresponds to inflammations of the skin hair follicles, forming a papulopustule. Reference is also made to folliculitis under the general term acneiform eruptions, although the latter clearly differ from acne due to the absence of comedones but also their possible location on the scalp. They appear very rapidly after the beginning of treatment and most commonly in sebhorreic areas such as the scalp, the face, the neck, the top of the back or else the chest, before possibly propagating to other skin areas. The latter may be more or less severe and may also be accompanied by pruritus and pain, but may also be complicated by bacterial infections in particular by *Staphylococcus aureus*. This folliculitis is thus part of the toxic cutaneous effects most commonly observed in patients undergoing anti-cancer treatment and in particular subjected to targeted therapies, that is to say therapies specifically directed against molecular targets supposed to play a role in neoplastic transformation of the cancer cell.

By way of example of targeted therapies, agents which inhibit epidermal growth factor receptors (EGFRs) are commonly used for treating solid tumors. The agents which have an anti-EGFR activity are either monoclonal antibodies or tyrosine kinase inhibitors. Indeed, the activation of epidermal growth factor receptors activates the signaling pathways responsible for cell proliferation and survival. These receptors are involved in the oncogenesis of numerous solid tumors, and are in particular overexpressed by malignant cells.

Since epidermal growth factor receptors are widely expressed within the epidermis, the use of anti-EGFR agents is often accompanied by numerous toxic cutaneous effects and in particular by folliculitis, observed in more than 85%. This folliculitis can also be caused by other therapeutic agents used in targeted therapy, such as selective inhibitors of a protein kinase activated by mitogenic agents, such as MEK1 and/or MEK2 kinases. These MEK-inhibiting agents target the MAPK/ERK signaling pathway which is very often hyperactive in certain cancers. These MEK inhibitors can in particular used in the treatment of melanomas and colorectal cancers. The appearance of these papulopustular eruptions is observed in more than 90% of patients treated using MEK inhibitors.

Given the very high occurrence of this folliculitis, the severity of some forms and of the not only physical but also psychological discomfort of the patient, it is sometimes necessary to limit the doses of these anti-cancer agents and sometimes even to interrupt the therapy, thus endangering the efficiency of the treatment recommended by the physician and thus the patient's health.

For this reason, it is necessary to find a solution which makes it possible to treat and/or prevent the appearance and/or worsening of folliculitis caused by anti-cancer agents and more particularly by those used in targeted therapy.

There are solutions which exist today, such as the use of benzoyl peroxide, of oral or topical antibacterial agents such as tetracyclines, or else of retinoic acids. On the other hand, the efficacy of these treatments is anecdotal and has not been officially demonstrated. In addition, side effects which are sometimes not insignificant can be observed with the use of these agents for treating and/or preventing this folliculitis. Thus, retinoids can lead to dryness of the skin, irritations, erythema, desquamation and stinging or burning for the patients treated. The use of such treatments thus also requires the application of multiple moisturizers, humectants and soothing agents in order to soothe the patient. Oral and/or local corticosteroids can be used in the most severe cases, but the latter have a high risk of interfering with the efficacy of the anti-cancer agents. The taking of antibiotics such as tetracycline, erythromycin, minocycline and doxycycline for treating this drug-related folliculitis is also recommended, but their low lipid solubility requires regular and frequent administration which can cause bacterial resistance phenomena and promote the development of these resistant organisms, and also problems of intolerance in the patient, in particular photosensitivity or else digestive problems.

Solutions for prophylactic purposes are also proposed in the prior art, but their efficacy is unsatisfactory. The oral use of tetracyclines and more particularly of doxycycline once a day is the prophylactic solution most commonly used, but it only makes it possible to reduce the severity of the papulopustular eruptions and not to prevent their occurrence.

There are certain means for combating the worsening of folliculitis in the presence of skin pathogens, in particular the use of chemical antibacterial agents or of antibiotics such as penicillin or ampicillin, which are the most commonly used. However, these solutions have a certain number of drawbacks because *Staphylococcus aureus* rapidly becomes resistant to antibiotics. Although published patent application FR2740039 describes the use of a substance chosen from aldehydes and bifunctional agents, preferably glutaraldehyde, for inhibiting the binding of pathogenic strains such as *Staphylococcus aureus* to keratinocytes and corneocytes, these treatments are generally expensive and harmful both to the health and to the environment.

In the light of the above statement, there is a considerable need to find an effective solution which makes it possible to treat and/or prevent the appearance of folliculitis, but also the complications thereof such as bacterial superinfections. More particularly, it is necessary to provide an effective solution for treating and/or preventing the appearance of folliculitis caused by anti-cancer agents and more specifically by targeted-therapy agents while at the same time limiting the side effects observed in the prior art.

SUMMARY OF THE INVENTION

The inventors propose to use compounds of the avermectin family and preferably ivermectin for treating and/or preventing, preferably topically, folliculitis caused by anti-cancer agents and also the potential worsening thereof in the presence of bacteria such as *Staphylococcus aureus*.

The present invention relates more generally to compounds of the avermectin family for use in the treatment and/or prevention of folliculitis caused by anti-cancer agents and more particularly by targeted-therapy agents. It also relates to a pharmaceutical composition, preferably intended for topical administration, comprising the compound of the avermectin family, for use in the treatment and/or prevention of folliculitis caused by anti-cancer agents and more particularly targeted-therapy agents.

In one preferred embodiment, the compound of the avermectin family is ivermectin.

DETAILED DESCRIPTION OF THE INVENTION

Anti-cancer treatments and more particularly targeted therapies cause numerous side effects, in particular at the cutaneous level. Among the toxic cutaneous effects most commonly observed are papulopustular eruptions, also called folliculitis. This folliculitis is in particular observed in patients undergoing chemotherapy treatment and more particularly "targeted" therapies. Reference may in particularly made to targeted-therapy agents which have an inhibitory activity on epidermal growth factor receptors (EGFRs) or else to selective inhibitors of a protein kinase activated by mitogenic agents such as MEK1 and/or MEK2 kinases.

The term "folliculitis" is intended to mean papulopustular eruptions observed at the level of the hair follicles, in particular at the level of sebhorreic areas such as the face, the neck, the back, the torso or else the scalp. It is often accompanied by pruritus and by erythematous lesions, but is never associated with comedones, thus making possible to clearly distinguish it from acne. It is possible to distinguish three different grades of folliculitis severity, grade 1 corresponding to the appearance of papules, grade 2 corresponding to the appearance of papules and pustules and, finally, grade 3 corresponding to the appearance of papules and pustules accompanied by pruritus and skin pain. Folliculitis shares certain similarities with rosacea, but clearly differs therefrom by a certain number of characteristics. Indeed, contrary to rosacea, folliculitis caused by chemotherapy treatments appears abruptly as soon as the treatment is introduced and is gradually or abruptly spontaneously resolved as soon as the treatment is stopped. Moreover, contrary to rosacea, which is observed essentially on the face, folliculitis generally extends to all seborrheic areas, in particular on the face, the scalp, the back and the trunk.

Folliculitis is observed in more than 85% of patients undergoing these anti-cancer treatments and in particular targeted therapies, this being quite rapidly since it generally appears after 7 to 15 days. This folliculitis caused by anti-cancer treatment may also be followed by superinfection by *Staphylococcus aureus* bacteria thus worsening the severity of the folliculitis observed. The severity of this folliculitis varies from one patient to an other. However, it is necessary to interrupt the anti-cancer treatment in approximately 15% of patients presenting this folliculitis.

Recent studies have made it possible to demonstrate the key mechanisms involved that are responsible for folliculitis caused by anti-cancer agents and in particular by agents which have an anti-EGFR activity. It has in fact been demonstrated that the inhibition of the epidermal growth factor receptor induces the expression of numerous pro-inflammatory chemokines such as CCL2, CCL5, CCL27 or else CXCL14, but also of cytokines such as those belonging to the IL-1 family responsible for the recruitment of inflammation cells (T cells, Langerhans cells, mast cells, macrophages, granulocytes) within the perifollicular area generating follicular papules and pustules. A significant decrease in the expression of barrier genes (claudin, occludin) and of antimicrobial peptides (LL37, HBD3, RNase 7) leading to dryness of the skin and an increased risk of bacterial infections, in particular by *Staphylococcus aureus* (Lichtenberger et al., Sci Transl Med, 2013, 5: 199ra111). These biological mechanisms clearly differ from those involved in patients suffering from rosacea for whom T-cell activation has been demonstrated, combined with the production of the IL17 and IL22 cytokines, enabling the attraction of specific chemokines such as CXCL1, CXCL8, CCL20 and CCL2 (Gerber et al., Journal of Investigative Dermatology Symposium Proceedings 15, 40-47; 2011).

As previously specified, the anti-cancer agents which frequently cause folliculitis are in particular those used for "targeted" therapies. By way of example, reference may be made to agents which have an anti-EGFR activity, but also agents which are selective inhibitors of a protein kinase activated by mitogenic agents, such as MEK1 and/or MEK2 kinases.

For the purposes of the present invention, the term "anti-cancer agents" is intended to mean any chemical substance of which the objective is to treat cancer; consequently encompassed in this definition are "chemotherapy agents" termed conventional and also "targeted-therapy agents".

For the purposes of the present invention, the term "chemotherapy agents" is intended to mean any chemical substance of which the objective is to treat cancer by means of a general action aimed at affecting cell division, in particular by interacting with the essential structures of cell division and survival.

For the purposes of the present invention, the term "targeted-therapy agents" is intended to mean any chemical substance of which the objective is to treat cancer by specifically targeting a receptor, a gene or a protein involved in the intracellular signaling pathway(s) which play a role in the transformation of normal cells into cancer cells or in the development of malignant tumors. More specifically, the targeted-therapy agents may be monoclonal antibodies targeting a specific cell receptor or else a molecule capable of binding to one of these receptors or else small tyrosine-kinase-inhibiting molecules capable of inhibiting cell signaling pathways.

For the purposes of the present invention, the term "monoclonal antibodies" is intended to mean an antibody specifically directed against a "target" which may for example be the extracellular part of a receptor at the surface of the cells. Reference is in particular made to bevacizumab which targets vascular endothelial cell growth factor (VEGF), or else to cetuximab which targets epidermal growth factor (EGF) cell receptors, or else to panitumumab which has the same mode of action as cetuximab and is indicated in the absence of K-Ras mutation. Reference may also be made to brentuximab, catumaxomab, ibritumomab, ipilimumab, ofatumumab, rituximab, or else to trastuzumab.

For the purposes of the present invention, the term "small tyrosine-kinase-inhibiting molecules" refers in particular to agents capable of penetrating inside cancer cells and of affecting the cell signaling pathways involved in malignant cell growth. For the purposes of the present invention, mention may be made of axitinib, crizotinib, dasatinib, erlotinib, gefitinib, imatinib, lapatinib, nilotinib, ruxolitinib, sorafenib, sunitinib, vandetanib, vemurafenib, everolimus, regorafenib or else temisrolimus.

For the purposes of the present invention, the term "agents which have an anti-EGFR activity" refers in particular to the families of agents which inhibit the epidermal growth factor EGF transduction pathway. Said agents are in particular small kinase-inhibiting molecules and/or else EGFR-inhibiting monoclonal antibodies. More specifically, reference is made to cetuximab, to gefitinib, to erlotinib, to panitumumab and/or to lapatinib.

The term "agents which are selective inhibitors of a protein kinase activated by mitogenic agents" also called "MEK inhibitors" in the present invention, refers to agents which are selective inhibitors of a protein kinase activated by mitogenic agents such as MEK1 and/or MEK2 kinases, for example trametinib, selumetinib, binimetinib or cobimetinib.

Surprisingly, the applicant has been able to demonstrate that a compound of the avermectin family, preferentially ivermectin, for topical use makes it possible to effectively treat and/or prevent folliculitis caused by anti-cancer agents.

The subject of the present invention thus relates to a compound of the avermectin family, preferentially ivermectin, for use in the treatment and/or prevention of folliculitis caused by anti-cancer agents.

According to another aspect, the present invention also relates to a compound of the avermectin family, preferentially ivermectin, for use in the treatment and/or prevention of folliculitis caused by anti-cancer agents and also the potential worsening thereof in the presence of bacteria such as Staphylococcus aureus.

For the purposes of the present invention, the anti-cancer agents responsible for folliculitis are preferably the agents used in targeted therapies. According to one preferred embodiment, said agents used in targeted therapies are those which have an anti-EGFR activity and the MEK inhibitors as defined above.

The present invention also relates to a pharmaceutical composition comprising a compound of the avermectin family, preferentially ivermectin, in the presence of a pharmaceutically acceptable support, for use in the treatment and/or prevention of folliculitis caused by anti-cancer agents.

According to another aspect, the present invention also relates to a pharmaceutical composition comprising a compound of the avermectin family, preferentially ivermectin, in the presence of a pharmaceutically acceptable support, for use in the treatment and/or prevention of folliculitis caused by anti-cancer agents and also the potential worsening thereof in the presence of bacteria such as Staphylococcus aureus.

The invention also relates to methods using a composition comprising a compound of the avermectin family, preferentially ivermectin, for topical administration, in a therapeutically effective amount in a patient suffering or possibly suffering from folliculitis caused by anti-cancer agents.

According to one embodiment, the present invention relates to a treatment method consisting in topically administering a composition comprising a compound of the avermectin family, preferentially ivermectin, in an effective amount in a patient suffering from folliculitis caused by anti-cancer agents.

According to another embodiment, the present invention also relates to a prevention method consisting in topically administering a composition comprising a compound of the avermectin family, preferentially ivermectin, in an effective amount simultaneously with the administration of the anti-cancer agent. The composition comprising a compound of the avermectin family, preferentially ivermectin, and the anti-cancer agents can be administered simultaneously via the same route of administration or via two different routes of administration. Preferably, the composition according to the present invention is administered topically.

For the purposes of the present invention, the anti-cancer agents are preferably the agents used in targeted therapies.

The avermectin family is a group of macrocyclic lactones produced by the Streptomyces avermitilis bacterium (Reynolds JEF (Ed.) (1993) Martindale. The extra pharmacopoeia. 29th Edition. Pharmaceutical Press, London). Among these macrocyclic lactones belonging to the avermectin class, mention may be made of ivermectin, avermectin, abamectin, doramectin, eprinomectin, la selamectin, or aversectin B, AB or C. According to the invention, the compound of the avermectin family is preferably ivermectin.

Ivermectin is a mixture of 22,23-dihydroavermectin $B_{1a}$ and 22,23-dihydroavermectin $B_{1b}$. Ivermectin predominantly contains 22,23-dihydroavermectin $B_{1a}$.

Ivermectin is known in the prior art for its antiparasitic properties, in particular against Demodex, and antihelmintic properties. In the middle of the 1980s, the molecule was presented as a broad-spectrum antiparasitic medicament for veterinary use (W. C. Campbell et al., (1983). Ivermectin: a patent new antiparasitic agent. Science, 221, 823-828.). It is efficacious against most common intestinal worms (except for tapeworms), most acarids, and some lice. It has a high affinity for glutamate-dependent chloride channels, in particular those which are dependent on the neuromediator GABBA (gamma-aminobutyric acid), present in invertebrate nerve and muscle cells, conferring on it antiparasitic activity. More particularly, its binding to these channels promotes an increase in membrane permeability to chloride ions leading to hyperpolarization of the nerve or muscle cell. This results in neuromuscular paralysis which can lead to the death of certain parasites. Ivermectin also interacts with other chlorine channels.

Ivermectin has also been used in the treatment of acne vulgaris. U.S. Pat. No. 6,399,652 describes the use of ivermectin in the treatment of acne as a supplement to another composition containing another active agent which may be benzoyl peroxide, resorcinol, salicylic acid, an opioid, tertinoin, an antibiotic or isotretinoin.

Ivermectin also makes it possible to reduce and eliminate the parasite Demodex for which an increase in its density has been observed in patients suffering from acne (Zhao et al., J Zhejiang Univ Sci B., 2012, 13, 192-202).

Without wishing to be bound by any theoretical explanation regarding the mode of action and the efficacy of the compounds, the invention takes advantage of the anti-inflammatory properties of the compounds of the avermectin family and also their antiparasitic properties, in particular with respect to Demodex. Indeed, the compounds of the avermectin family are effective anti-inflammatory agents capable of blocking certain inflammation mediators and thus of decreasing the symptoms caused by inflammation.

In one particular embodiment, the compound of the avermectin family, preferentially ivermectin, is present in the composition between 0.001% and 10%, preferentially between 0.001% and 8%, preferably between 0.001% and 5%, even more preferentially between 0.1% and 3%, more preferably between 0.1% and 2%, and even more preferably 1% by weight, relative to the total weight of the composition.

In one preferred embodiment, the composition according to the present invention comprising the compound of the avermectin family, preferentially ivermectin, is administered simultaneously with the anti-cancer agents. The composition according to the invention and the anti-cancer agents can be administered via the same route of administration or via two different routes of administration.

The term "topically" is intended to mean administration to the skin, the skin appendages or the mucous membranes. More specifically, the pharmaceutical compositions based on compounds according to the invention are intended for the treatment of the skin and more preferentially in areas rich in hair follicles.

The useful compositions according to the invention may be in the form of emulsions, salves, creams, milks, lotions, ointments, powders, impregnated pads, solutions, gels, sprays, lotions, suspensions, soap or shampoos. They may also be in the form of lipid or polymeric microspheres, nanospheres or vesicles or polymer patches and hydrogels allowing a controlled release. These topically administered compositions may be either in anhydrous form or in aqueous form depending on the clinical indication. The present invention is more particularly directed toward a pharmaceutical composition containing, in a pharmaceutically acceptable carrier, at least one compound of the avermectin family as defined above. The compound of the avermectin family is preferably ivermectin.

In the useful compositions according to the invention, the compound of the avermectin family, and preferably ivermectin, can be combined with other pharmaceutical or cosmetic compounds, alone or as a mixture, such as retinoids, corticosteroids, non-steroidal anti-inflammatories, antibiotics or antifungal agents. The pharmaceutical compositions according to the invention can also contain inert additives or combinations of these additives and in particular: wetting agents, depigmenting agents, emollients, moisturizing agents, stabilizers, moisture-content regulators, pH regulators, osmotic pressure modifiers, emulsifiers, UV-A and UV-B screening agents, and antioxidants.

According to one preferred embodiment, the composition comprises one or more compounds of the avermectin family, one or more solvents, a fatty phase, one or more surfactants, and water.

Those skilled in the art will take care to select the additives and excipients constituting the compositions according to the invention according to the desired galenic form and such that the advantageous properties of the composition according to the invention are respected.

The present invention also relates to the use of the pharmaceutical composition according to the present invention, for treating and/or preventing folliculitis caused by anti-cancer agents.

According to one preferred embodiment, the pharmaceutical composition according to the present invention, for treating and/or preventing folliculitis caused by anti-cancer agents, is administered at the same time as said anti-cancer agents.

According to another embodiment, the present invention also relates to the use of the pharmaceutical composition according to the present invention, for treating and/or preventing the worsening of said folliculitis, through the proliferation of skin pathogens such as *Staphylococcus aureus*.

In one embodiment, the term "treatment" or "treating" denotes an improvement, prophylaxis, or the reversion of the folliculitis, or at least one symptom associated with the folliculitis. In another embodiment, "treatment" or "treating" denotes an improvement, prophylaxis, or the reversion of at least one measurable physical parameter associated with the folliculitis, which is not necessarily discernible in or by the subject treated. In another additional embodiment, "treatment" or "treating" denotes the inhibition or slowing down of the progression of the folliculitis, physically, for example, the stabilization of a symptom which is discernible, physiologically, for example, the stabilization of a physical parameter, or both. In another embodiment, "treatment" or "treating" denotes delaying the appearance of the folliculitis or of a symptom which is associated therewith.

In the present context, "prevention" or "preventing" denotes a reduction in the risk of acquiring folliculitis, but also a reduction, an inhibition ora slowing down of the appearance of the symptoms associated with folliculitis. Symptoms characteristic of folliculitis are, for example, papules or else pustules at the level of the hair follicles, erythemas, pustules, erythematous lesions or else pruritus appearing mainly on the face, the neck, the scalp, the back and the thorax, i.e. the skin regions where the largest number of sebaceous glands are found.

For the purposes of the present invention, the term "patient" is intended to mean any mammal, and more particularly human beings, men or women.

The amount actually administered of compound of the avermectin family, preferentially of ivermectin, to be used according to the invention depends on the desired therapeutic or preventive effect, and thus can vary to a large extent. Those skilled in the art, in particular the physician, can readily, on the basis of their general knowledge, determine the appropriate amounts.

Thus, and according to one preferred embodiment, the composition is administered once to twice/day for a therapeutic effect. Preferably, the treatment can have a duration ranging from 1 week to 6 months, which can be repeated, and preferably from 2 weeks to 4 months. The treatments can be repeated in a cycle with or without rest period. The administration of the composition according to the invention may or may not be simultaneous with the administration of the anti-cancer agents.

Thus, and according to another preferred embodiment, the composition is administered once to twice/day and simultaneously with the anti-cancer agents for a preventive effect. Preferably, the treatment can have a duration ranging from 1 week to 6 months, which can be repeated, and preferably from 2 weeks to 4 months. The treatments can be repeated in a cycle with or without rest period.

According to another preferred embodiment, the composition according to the present invention is administered simultaneously with the anti-cancer agents. The composition comprising a compound of the avermectin family, preferentially ivermectin, and the anti-cancer agents can be administered simultaneously or sequentially. Preferably, according to the present invention, the composition comprising a compound of the avermectin family, preferentially ivermectin, and the anti-cancer agents are administered simultaneously.

The administration of said composition and of the anti-cancer agents can be carried out via one and the same route of administration or via two different routes of administration. Preferably, the composition according to the present invention is administered topically.

In the context of the invention, the term "effective therapeutic dose" or "effective therapeutic amount" is intended to mean the dose, the therapeutic amount which prevents, eliminates or reduces the harmful effects of folliculitis treated in the patient. It is understood that the dose administered can be adjusted by those skilled in the art according to the patient, the severity of the folliculitis, the mode of administration, etc.

The example and the figures illustrate the invention without limiting the scope thereof.

EXAMPLE

A study was carried out on primary human keratinocytes in vitro, in order to determine the effect of ivermectin on the regulation of genes of which the expression has been identified as being modulated by EGFR inhibitors. Said genes identified are the pro-inflammatory chemokines CCL2, CCL5, CCL27 and CXCL14 and the cytokines of the IL-1β family, but also the genes of antimicrobial peptides RNase7, HBD3 and LL37.

Another objective of the present study was to identify the effect of ivermectin on the CXCL14 and CCL5 protein level of To do this, primary human keratinocytes were cultured with various concentrations of EGFR inhibitor (in this case erlotinib) each with +/− TNF-α/IL-1β, various concentrations of ivermectin alone each with +/− TNF-α/IL-1β various concentrations of erlotinib and of ivermectin each with +/− TNF-α/IL-1β. The addition of the pro-inflammatory cytokines TNFα and IL1β makes it possible to mimic the skin inflammation.

The various concentrations used were the following:
Erlotinib: 0-0.1 μM-1 μM-10 μM (each with +/− TNF-α/IL-1β)
Ivermectin: 0-0.1 μM-1 μM-10 μM (each with +/− TNF-α/IL-1β)
Co-stimulation:
Erlotinib (0.1 μM)+Ivermectin (1 μM) (+/− TNF-α/IL-1β)
Erlotinib (0.1 μM)+Ivermectin (5 μM) (+/− TNF-α/IL-1β)
Erlotinib (1 μM)+Ivermectin (1 μM)+/− TNF-α/IL-1β)
Erlotinib (1 μM)+Ivermectin (5 μM) (+/− TNF-α/IL-1β)

The expression of the CXCL14, CCL5 (chemokines), RNase 7, HBD3 and LL37 (antimicrobial peptides) genes was analyzed by quantitative PCR. The protein concentration of the chemokines CXCL14 and CCL5 was quantified using an ELISA assay.

Figure 1:
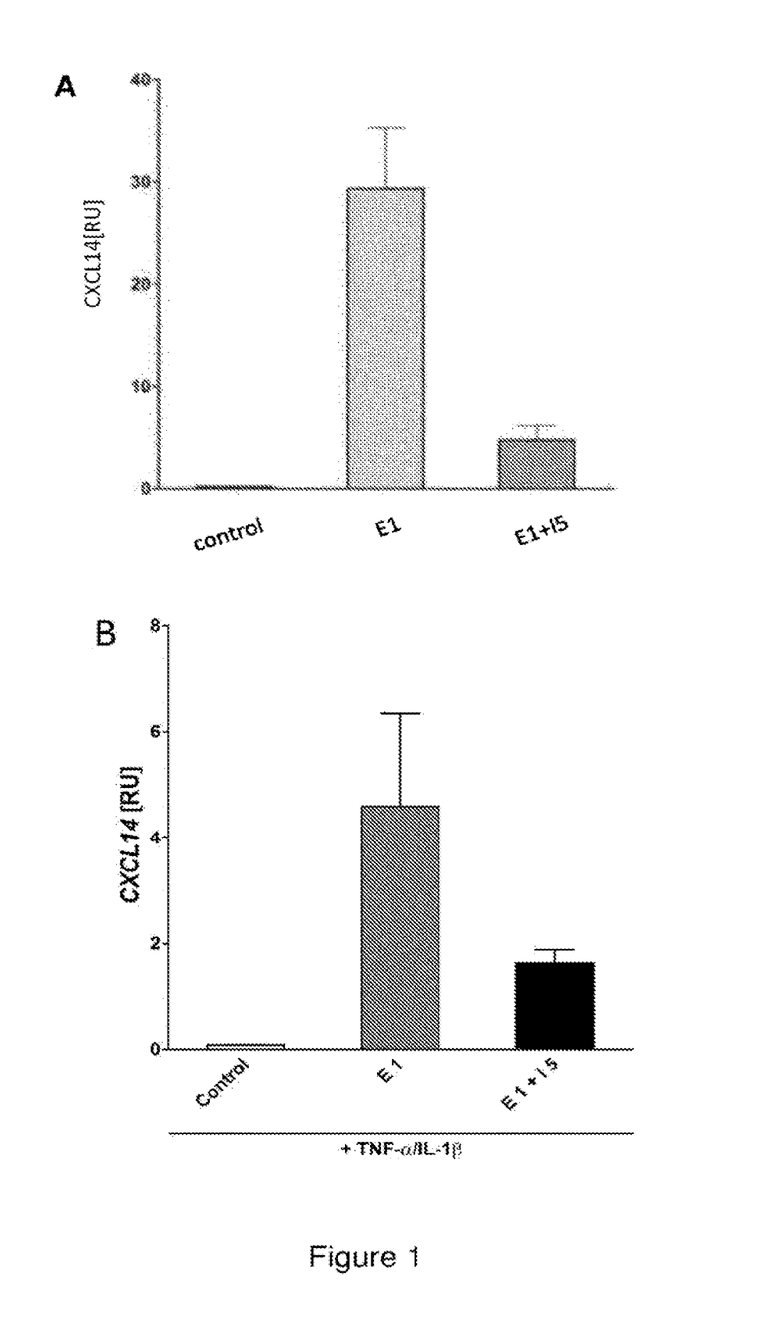
FIG. 1: Analysis of CXCL14 expression by keratinocytes treated with erlotinib alone or in combination with ivermectin (A), or with erlotinib alone or with ivermectin, in the presence of TNFα/IL1β (B). E1=erlotinib, 1 μM; I5=ivermectin, 5 μM.
Figure 2:
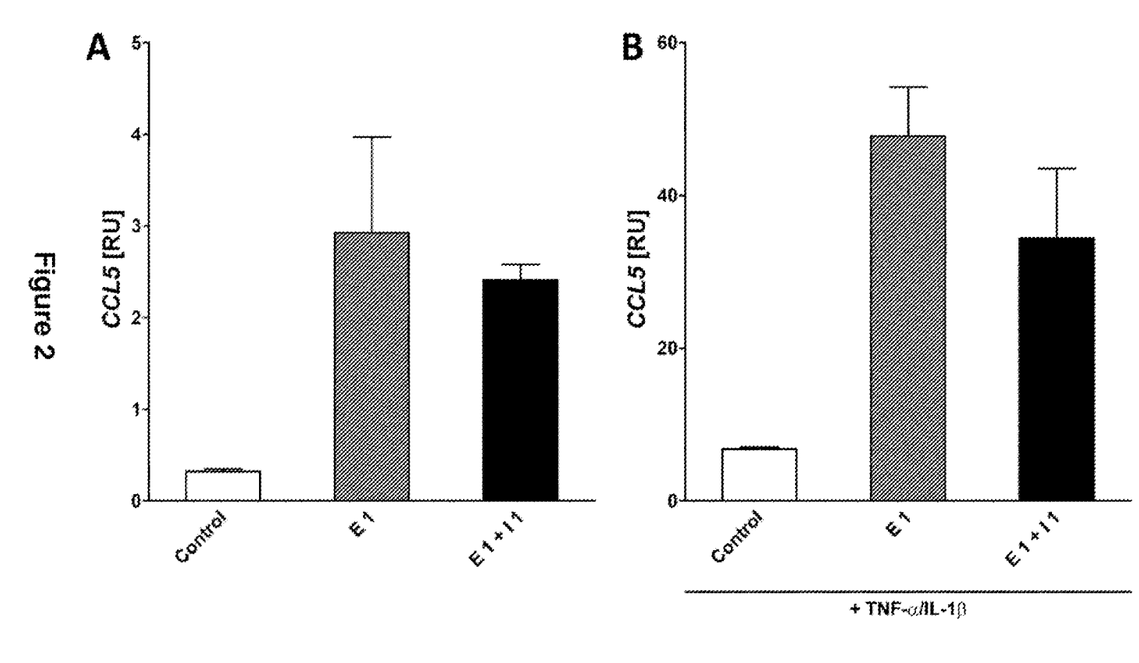
FIG. 2: Analysis of CCL5 expression by keratinocytes treated with erlotinib alone or in combination with ivermectin (A), or with erlotinib alone or with ivermectin, in the presence of TNFα/IL1β (B). E1=erlotinib, 1 μM; I1=ivermectin, 1 μM.
Figure 3:
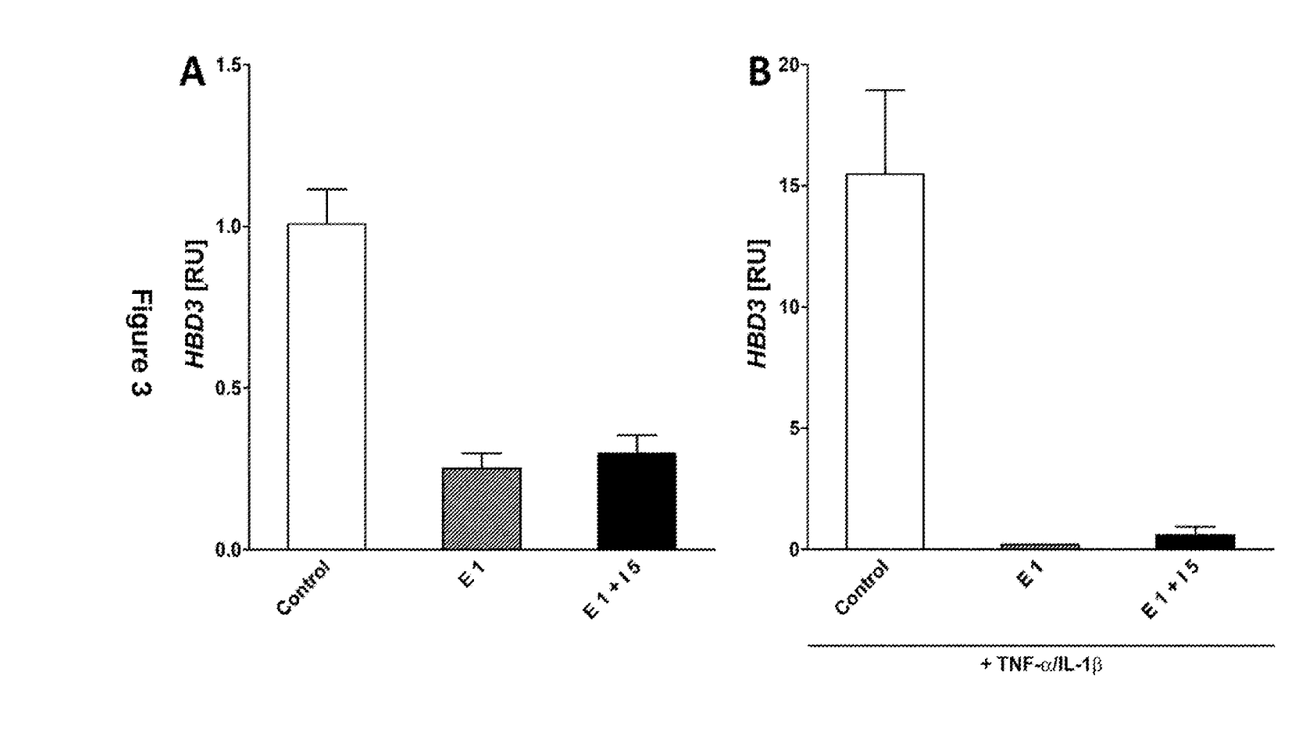
FIG. 3: Analysis of HBD3 expression by keratinocytes treated with erlotinib alone or in combination with ivermectin (A), or with erlotinib alone or with ivermectin, in the presence of TNFα/IL1β (B). E1=erlotinib, 1 μM; I5=ivermectin, 5 μM.

Results:

The treatment of the primary human keratinocytes with erlotinib alone or in the presence of ivermectin+/− TNFα/IL1β made it possible to demonstrate a clear increase in the expression level of the CCL5 and HBD3 genes in the presence of TNFα/IL1β and a significant modification of the induction, by erlotinib, of the expression of CXCL14 and CCL5 in the presence of ivermectin.

These tests showed the capacity of ivermectin to reduce the overexpression of CCL5 and CXCL14 induced by erlitonib but also to induce the expression of HBD3 decreased in the presence of erlotonib.

Figure 4:
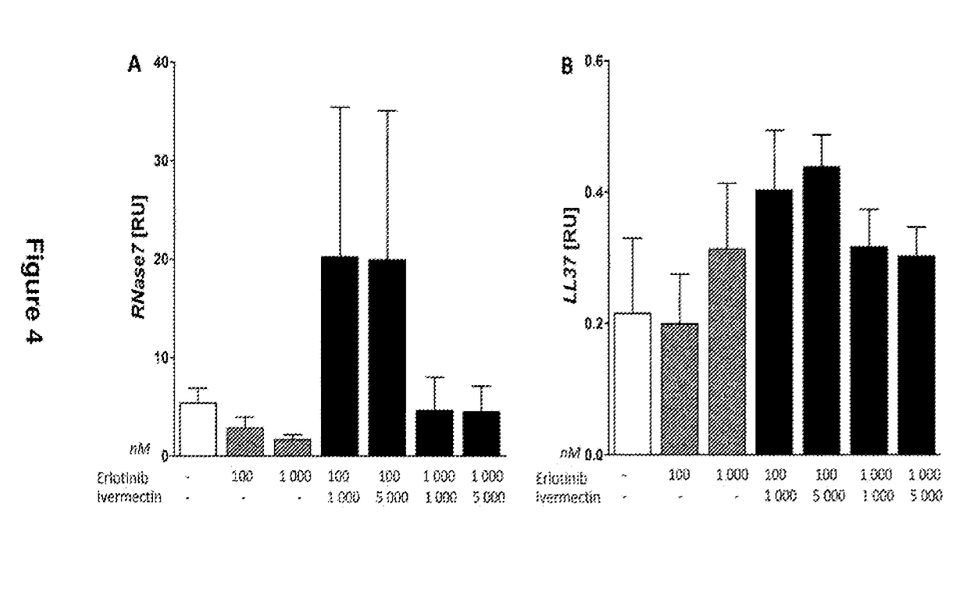
FIG. 4: Analysis of the expression of RNase 7 (A) and of LL37 (B) by primary human keratinocytes treated with various concentrations of erlotinib alone or in combination with ivermectin at various concentrations.

Ivermectin also makes it possible to re-establish the expression of RNase 7 greatly decreased in the presence of erlotinib but also to induce a strong expression thereof. To a lesser extent, the same effects were observed for LL37.

Figure 5:
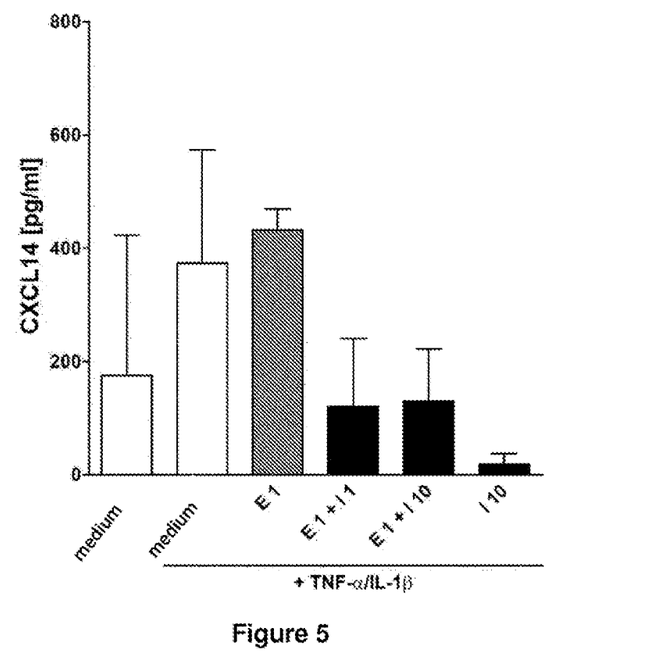
FIG. 5: Analysis of the CXCL14 protein level with the ELISA assay in primary human keratinocytes treated with erlotinib alone or in combination with ivermectin at various concentrations. E1=erlotinib, 1 μM; I1=ivermectin, 1 μM; I10=ivermectin, 10 μM.
Figure 6:
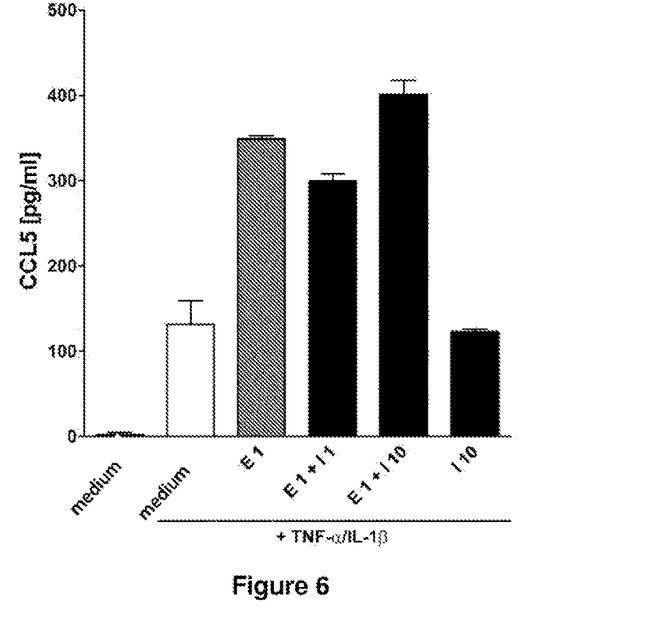
FIG. 6: Analysis of the CCL5 protein level with the ELISA assay in primary human keratinocytes treated with erlotinib alone or in combination with ivermectin at various concentrations. E1=erlotinib, 1 μM; I1=ivermectin, 1 μM; I10=ivermectin, 10 μM.

These assays also made it possible to demonstrate an increase in CXCL14 and CCL5 protein concentration in the presence of erlotinib and of TNFα/IL1β and the capacity of ivermectin to decrease the protein level of CXCL14 and to a lesser extent of CCL5.

All of these results thus demonstrate the capacity of ivermectin to modify re-establish the basic expression profile of genes modulated by EGFR inhibitors, which reinforces its advantage for treating and/or preventing folliculitis caused by EGFR inhibitors but also the superinfection thereof by *Staphylococcus aureus*.

The invention claimed is:

1. A method of treating folliculitis caused by an anti-cancer agent, the method comprising administering an effective amount of a compound of the avermectin family to an individual subject in need thereof, wherein the folliculitis exhibits proliferation of *Staphylococcus aureus*.

2. The method as claimed in claim 1, wherein the anti-cancer agent is a chemotherapy agent or a targeted-therapy agent.

3. The method as claimed in claim 2, wherein the targeted-therapy agent is selected from the group consisting of agents which have an anti-EGFR activity and MEK-inhibiting agents.

4. The method as claimed claim 1, wherein the compound of the avermectin family is selected from the group consisting of ivermectin, avermectin, abamectin, doramectin, eprinomectin, selamectin, aversectin B, AB or C, emamectin B1b or latidectin.

5. The method as claimed in claim 1, wherein the compound of the avermectin family is ivermectin.

6. The method as claimed in claim 3, wherein the therapeutic agent having an anti-EGFR activity is selected from the group consisting of cetuximab, gefitinib, erlotinib, panitumumab lapatinib, and mixtures thereof.

7. The method as claimed in claim 3, wherein the MEK-inhibiting targeted-therapy agent is selected from the group consisting of trametinib, selumetinib, binimetinib and cobimetinib.

8. The method as claimed in claim 1, wherein the compound is a pharmaceutical composition.

9. The method as claimed in claim 8, wherein the composition is in a form suitable for topical administration.

10. The method as claimed in claim 9, wherein the composition is in the form of an emulsion, cream, lotion, gel, solution or salve.

11. The method as claimed in claim 1, wherein the composition comprises from 0.001% to 10% by weight of the compound of the avermectin family, relative to the total weight of the composition.

12. The method as claimed in claim 1, wherein the composition comprises 1% by weight of the compound of the avermectin family in comparison with the total weight of the composition.

13. The method as claimed in claim 11, wherein the composition comprises from 0.001% to 8% by weight of compound of the avermectin family.

14. The method as claimed in claim 11, wherein the composition comprises from 0.001% to 5% by weight of compound of the avermectin family.

15. The method as claimed in claim 11, wherein the composition comprises from 0.1% to 3% by weight of compound of the avermectin family.

* * * * *